United States Patent [19]

Costello

[11] Patent Number: 5,207,087
[45] Date of Patent: May 4, 1993

[54] SENSOR CALIBRATOR AND TEST APPARATUS

[75] Inventor: David J. Costello, Spring, Tex.

[73] Assignee: Optex Biomedical, Inc., The Woodlands, Tex.

[21] Appl. No.: 688,463

[22] Filed: Apr. 17, 1991

[51] Int. Cl.$^5$ .......................................... G01D 18/00
[52] U.S. Cl. ..................................... 73/1 G; 73/1 R; 204/427
[58] Field of Search ................. 73/1 R, 1 G; 204/401, 204/427, 428, 429, 435; 356/243; 250/252.1 R; 436/8–16, 19

[56] References Cited

U.S. PATENT DOCUMENTS

| | | | |
|---|---|---|---|
| 3,824,157 | 7/1974 | Macur | 73/1 G X |
| 4,119,406 | 10/1978 | Clemens | 422/81 |
| 4,201,222 | 5/1980 | Haase | 128/634 |
| 4,209,300 | 6/1980 | Thibault | 73/1 G X |
| 4,221,567 | 9/1980 | Clark et al. | 73/1 R X |
| 4,279,142 | 7/1981 | McIntyre | 73/1 R |
| 4,358,424 | 11/1982 | Weber et al. | 422/68 |
| 4,489,590 | 12/1984 | Haddon | 73/1 G |
| 4,531,398 | 7/1985 | Di Benedetto et al. | 73/1 G |
| 4,567,748 | 2/1986 | Klass et al. | 73/1 G |
| 4,635,467 | 1/1987 | Hoffa et al. | 73/1 G |
| 4,700,560 | 10/1987 | Hoffa et al. | 73/1 G |
| 4,704,893 | 11/1987 | Marsoner et al. | 73/1 G |
| 4,737,343 | 4/1988 | Hirschfeld | 422/63 |
| 4,739,645 | 4/1988 | Drbal | 73/1 G |
| 4,742,708 | 5/1988 | Porter | 73/1 G |
| 4,796,633 | 1/1989 | Zwirkoski | 128/634 |
| 4,823,167 | 4/1989 | Manska et al. | 356/243 |
| 4,834,532 | 5/1989 | Yount | 356/41 |
| 4,981,355 | 1/1991 | Higgins | 356/243 |
| 5,012,809 | 5/1991 | Shulze | 128/634 |
| 5,046,028 | 9/1991 | Bryan et al. | 204/401 X |

FOREIGN PATENT DOCUMENTS 2504677  10/1982  France.

OTHER PUBLICATIONS

"Technical Note," Medical & Biological Engineering & Computing, Nov. 1982, pp. 781–782.
"150 ion analyzer instruction Manual" Corning, 1984, particularly pp. 8–13 (pp. 1–21 provided).
"278 Blood Gas System Operator's Manual," Ciba--Corning, 1987, pp. 4–21 to 4–23.
"Controversies and Pitfalls in Arterial Blood Gas Monitoring," Optex Biomedical, Inc. (assignee of this invention). Published proceedings from the industry sponsored sessions associated with the 19th Annual Educational Scientific Symposium of the Society of Critical Corp. Medicine Jun. 1, 1990 San Francisco, Calif. pp. 1–15.

*Primary Examiner*—Tom Noland
*Attorney, Agent, or Firm*—Guy McClung

[57] ABSTRACT

Methods and apparatuses for testing chemical concentrations of fluids (liquids, gases) and for sensors used in such tests; methods and apparatuses for calibrating sensors and, in particular, for calibrating optical fiber sensors, the apparatus in one aspect including a body member with a cavity having gas inlet(s) and outlet(s) and a microporous tube therein for holding a fluid into which an optical probe sensor is insertable.

3 Claims, 3 Drawing Sheets

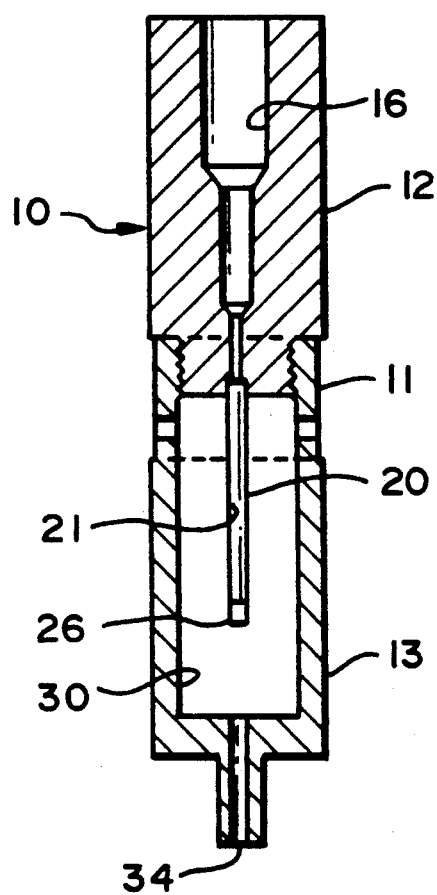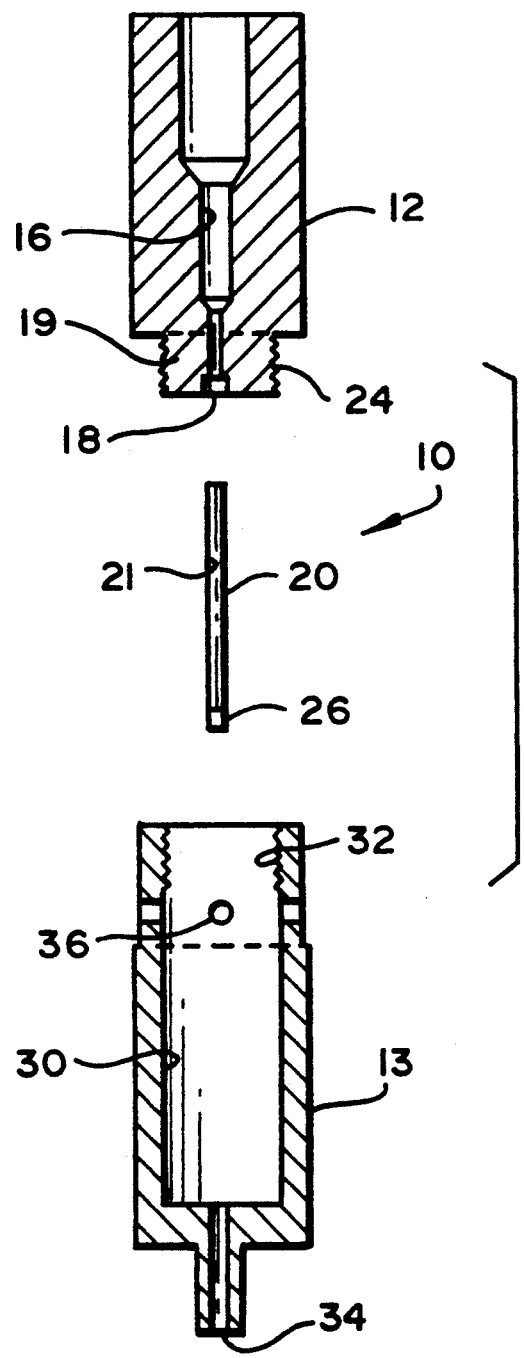
FIG. 1a
FIG. 1b

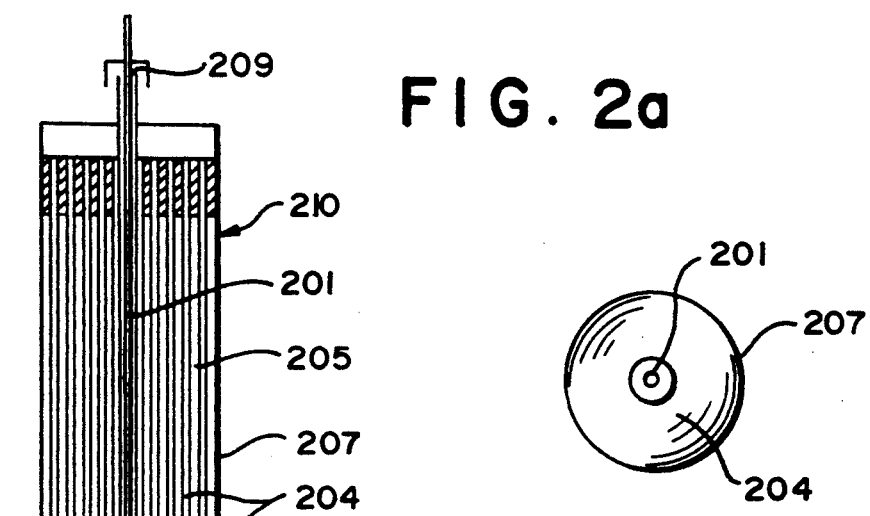
FIG. 2a
FIG. 2b
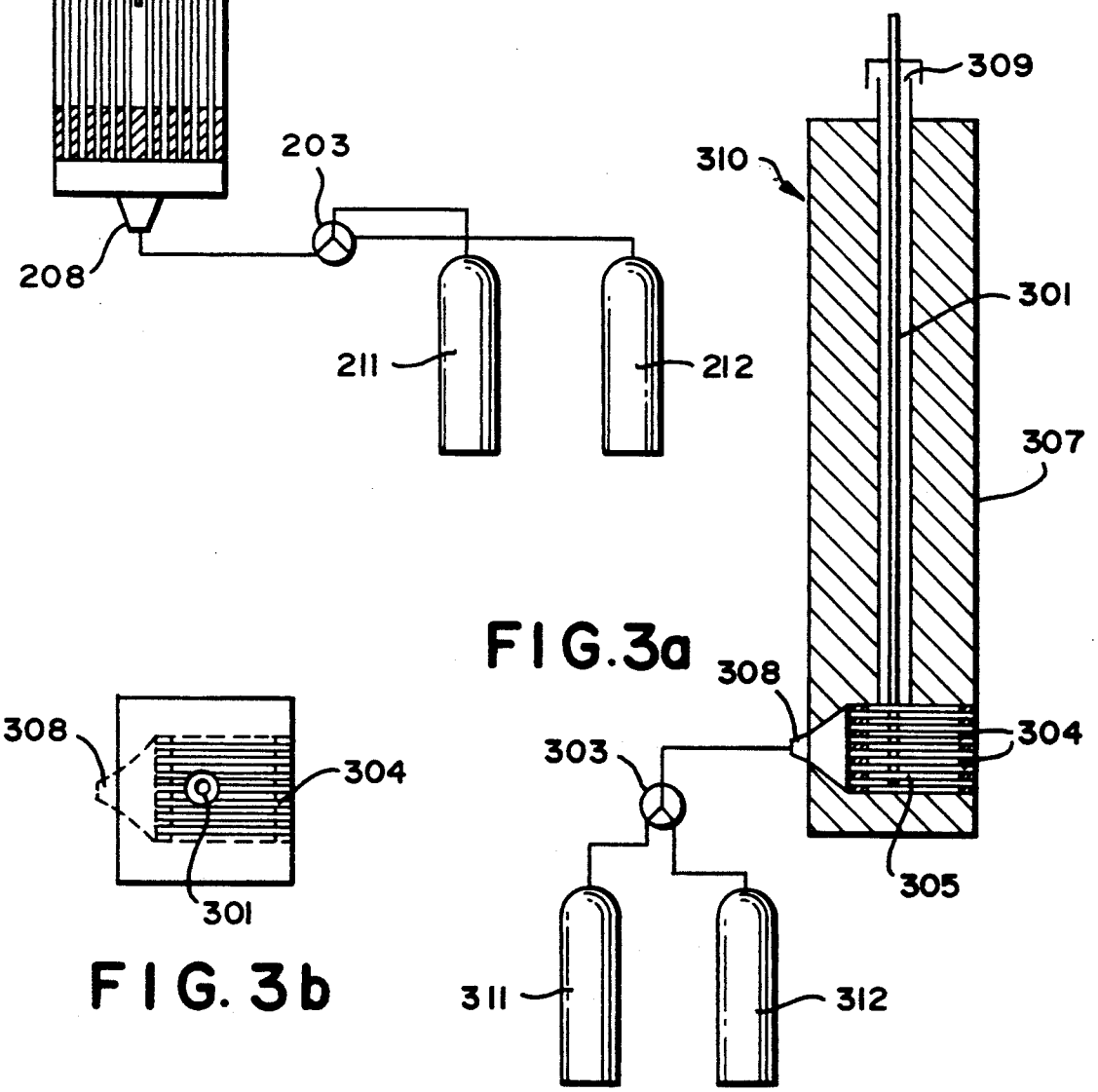
FIG. 3a
FIG. 3b

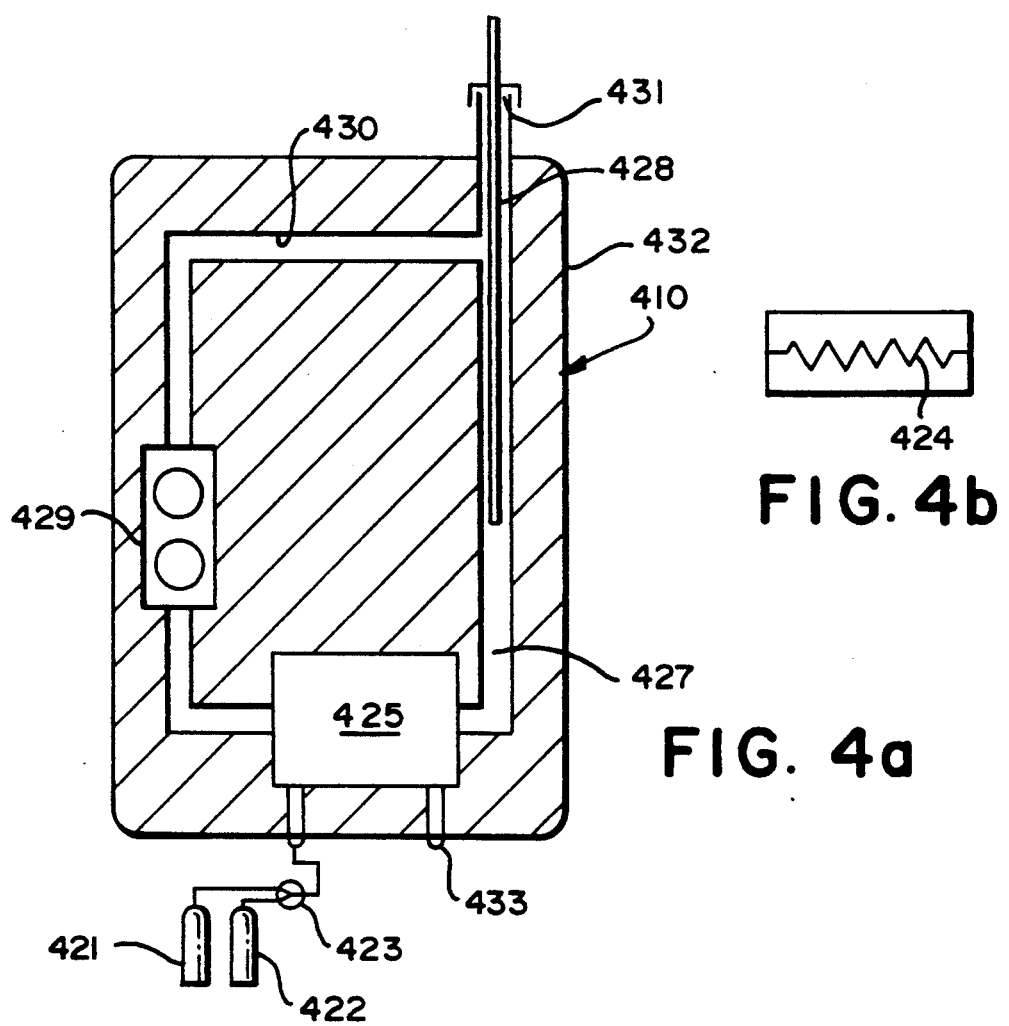
FIG. 4a
FIG. 4b
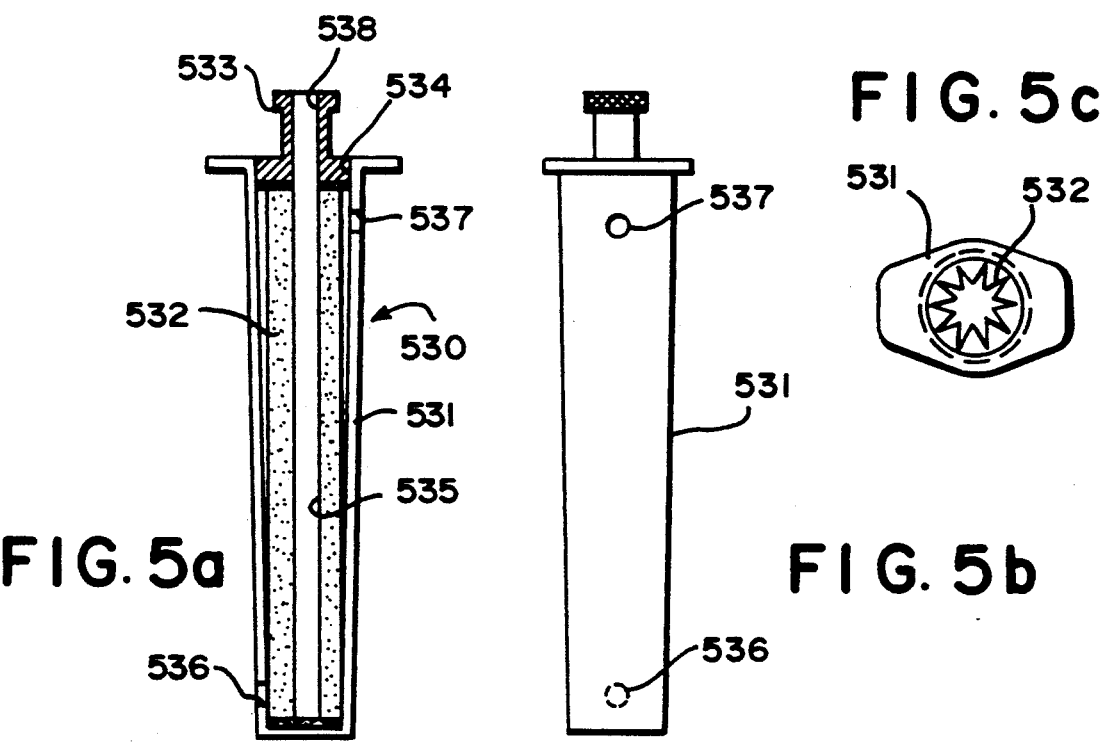
FIG. 5a
FIG. 5b
FIG. 5c

SENSOR CALIBRATOR AND TEST APPARATUS

BACKGROUND OF THE INVENTION

1. Field of the Invention

This invention is directed to: test apparatus into which a sensor test probe is insertable into a chemical to be tested; the calibration of sensors; to the maintenance of clean or sterile conditions during calibration; and, in one aspect, to optical blood gas sensor calibration devices and methods.

2. Description of Related Art

The prior art discloses a variety of chemical sensors including electrode sensors and electrical biosensors such as electrodes with a layer or layers of biological sensing material and electrodes with a particular sensing material (e.g., material that responds to the pH of a solution; material that responds to the oxygen concentration of a solution; and material that responds to the carbon dioxide concentration of a solution). These sensors are used in a fluid medium, in a gaseous medium, or in a fluid medium with gas diffused in it.

Sensors are calibrated to determine sensor response at two (or more) known analyte concentrations so that the value or level of an unknown concentration can be accurately predicted, measured, and displayed. Generally in the calibration of such sensors it is desirable to expose the sensor to a known medium while isolating it from the remainder of the environment. Often it is desired to maintain the sterility of a sensor during calibration to avoid the need for resterilizing the sensor before use. A variety of problems are encountered when a sensor is to be calibrated with respect to two or more analytes.

The prior art discloses a variety of methods and apparatuses for calibrating optical sensors. Non-clinical sensors are calibrated in multiple containers since sterile conditions and packaging are not a concern. Clinical laboratory sensors are generally calibrated by using a standardized sensor test fluid. For example, calibration of the Orion BOD sensor and Corning Limited 150 ion analyzer requires that an electrode calibrated in a first fluid (buffer) must be rinsed with a second fluid (buffer) or deionized water prior to immersing the electrode in the second buffer. Then the electrode is rinsed with a sample solution or deionized water to obtain a measurement for calibration. Another rinse step is required for each additional sample. Similar multiple rinsings are required for activity calibration. A similar machine that moves the fluid around instead of out of container is required for the machine-controlled calibration of the Ciba-Corning 278 Blood Gas System. Here again, sterility is not a problem.

In-line extracorporeal sensors are calibrated by bubbling a stream of gas through an aqueous solution in contact with the sensors. The sensor is then separated from the test solution (blood) by the addition of a semipermeable membrane to control infection.

Arterial blood gas measurement is one of the single most important laboratory tests of critically ill patients. Measurement of acid-base status, along with oxygen and carbon dioxide levels in arterial blood, is necessary to every medical specialist practicing in an intensive care unit; particularly in administering rational oxygen therapy, managing mechanical ventilation, and evaluating renal disturbances and shock. Inaccuracy in blood gas analysis can result from factors related to the operation and performance of the blood gas analyzer, including calibration techniques for use with optical blood gas sensors. There are a variety of problems with such sensors. For example, U.S. Pat. No. 4,739,645 discloses a complex device for calibrating blood gas sensors in which gas is bubbled through a two chambered vial which provides a recirculating mechanism to prevent fluid from leaving the device. The patent describes a calibration vial for storing and calibrating, under sterile conditions, a gas sensor that comprises an optical fiber whose sensing end carries a sensing element, such as a chromophore or fluorophore. The vial contains a calibrating liquid and is intended to keep the end of the sensor wet and permit fast calibration of the sensor without spillage of the calibrating liquid. The vial has a tubular inner calibration chamber in which the end of the fiber resides and which has a sterile filter-plugged gas inlet in its bottom and an outer concentric calibrating liquid reservoir chamber. The bottoms of the two chambers are interconnected by liquid reflux ports that are positioned so that gas coming into the bottom of the calibration chamber aspirates liquid from the reservoir chamber into the calibration chamber resulting in mixing and circulation of the liquid upwardly through the calibration chamber. The upper ends of the chambers are interconnected by a passageway through which liquid is returned to the reservoir and spent gas exits the calibration chamber. The spent gas is vented to the atmosphere via a vent that opens into the top of the reservoir chamber above the liquid level therein.

There has long been a need for an optical sensor calibrator in which known concentrations of a target substance are produced in the vicinity of a sensor and which eliminates the need for mixing volumes of fluids or changing containers to produce sequential known test solutions. There has long been a need for a calibration device which makes it possible to maintain the clean or sterile condition of a sensor during calibration. There has long been a need for such a sensor which is to be packaged in a static fluid container without the provision for adding an additional volume of fluid. There has long been a need for such a calibrator which does not require that a probe be transferred between multiple containers of premixed liquid solutions.

SUMMARY OF THE PRESENT INVENTION

The present invention, in one embodiment, is directed to a test container for a sensor for sensing chemical concentration in a second fluid, the test container having a body with a cavity in it for receiving a first fluid, a permeable member in the cavity which separates the first fluid from a second fluid, the body having an opening through which a probe of the sensor is insertable into the second fluid, the body having one or more inlets through which the first fluid flows into the cavity and passes through the member to diffuse into the second fluid for sensing by the sensor probe, and the body having one or more outlets through which the first fluid flows out of the cavity. If the chemical concentration of the first fluid is known, the test container may be used as a calibrator. As desired, the permeable member may be selectively impermeable to certain material in the first fluid, e.g. but not limited to bacteria, to preserve the cleanliness or sterility of the second fluid. The fluids may be either gas or liquid or a combination of them. In an alternative embodiment, rather than using the device as a calibrator with a second fluid of a know concentration, the device can be used as a test container, i.e., an apparatus with which the unknown concentration of a second fluid can be measured. It can also be used for measuring gas concentrations when using a gas concentration sensor which must be maintained in a wet environment. Thus the device may be used a calibrator, a test device, or both. In one embodiment the permeable member is a hollow tube made from microporous material and, if the probe is sterile, its sterility is maintained in the tube.

The present invention, in one embodiment, teaches a blood gas sensor calibrator that has a body member which is either a single integral piece or is comprised of two or more pieces that are secured together, e.g. by threaded connections. In one version having two members threadedly connected together, a first member has a channel therethrough and may have a female luer connector at one end thereof for facilitating disposition of a sensor probe mount with respect to the first member and for facilitating alignment of and insertion of the probe into the channel. At the other end of the channel, a hollow member such as a tube of a microporous material is sealingly connected at the channel opening so that the probe can also extend into a channel within the tube. A distal end of the tube is sealed shut, e.g. by crimping and/or with a sealant, e.g. an adhesive. Threads can be provided on an end of the first member for mating with corresponding threads on a second member. The second member has a cavity therein in which is disposed the tube and the probe enclosed therein. The second member has an inlet or inlets for introducing a gas of known identity and concentration (or a mixture of such gases) into the cavity. In one embodiment threads are at one end of the second member and the inlet(s) is at an opposite end. One or more gas outlets are provided in the body member to permit gas to flow from the cavity. In one embodiment this outlet(s) is provided through a wall of the second member. In another embodiment this outlet(s) is a channel(s) through the first member which is in communication with the cavity. The microporous tube is filled interiorly with a fluid, e.g., a physiological buffer solution. A removable plug may be used to close off the channel through the first member.

In operation, the described calibrator is used by removing the plug that closes off the channel through the first member and then a known fluid is introduced into the channel in the tube. A blood gas sensor probe is then inserted through the channel of the first member and into the channel in the microporous tube. A gas of known type and concentration is introduced into the cavity and it passes across the microporous tube, diffuses into the fluid inside the tube, and then interacts with the sensor probe extending into the tube's interior. The probe is interconnected with some type of monitoring/indicating system which provides a reading of a measurement of a value for the gas concentration. This measurement is used as a calibration point. Once a first reference point has been obtained, another gas of a different concentration or kind can be introduced into the cavity without the need for changing the fluid around the probe, without the need for changing the microporous material, and without the need for removing the probe and rinsing it. The microporous material permits only gas to flow into the tubes's interior and it prevents liquid from flowing out through the tube. Of course, it is within the scope of this invention: to employ multiple calibrators according to this invention; to remove a probe from one such calibrator and insert it into another; and to change the microporous tube on one calibrator and substitute for it a microporous tube of different parameters.

The present invention, in another embodiment, discloses a device for calibrating sensors that includes a fluid reservoir and a channel for a moving fluid stream containing the substance to be sensed in known concentration (e.g., but not limited to mixed gases), the two fluids being separated by a selectively permeable membrane. The sensor is placed in the reservoir close to the permeable membrane. The target substance diffuses across the membrane and reaches chemical equilibrium with the sensor environment. Provision of multiple compositions of the moving fluid produces a sequence of different equilibria near the sensor which provide points of reference for calibrating the response of the sensor.

In the case of a catheter probe for blood gas measurement, the reservoir may be a narrow tube filled with aqueous solution. The moving fluid may be a mixture of gases including oxygen and carbon dioxide. The permeable layer may be a number of microtubes composed of a gas permeable material. The permeable tubes may be arranged to closely surround the sensor active site. As gases flow through the tubes, they diffuse through the sides of the tubes and equilibrate with the sensor environment. By producing predetermined changes in the composition of the gas, various concentrations of gas are created near the sensor. The sensor response to these known changes is used to predict unknown concentrations in other environments such as the human bloodstream.

In certain embodiments of this invention, sensor sterility is preserved by the use of one container at constant volume. In addition the volume of fluid near the sensor may be minimized; and the distance between the sensor and the known fluid and the permeability and thickness of the separating membrane may be optimized so that the time required for calibration is reduced as compared with respect to the time required for devices using bubbles and/or convection for equilibration. The moving fluid may be a liquid, with permeability of the separatory membranes selected to allow diffusion of soluble substances such as ions or other compounds. The separatory membrane may be a flat sheet, a pleated sheet, or sheets with fluid flowing on either side. A pump may be used to circulate the known fluids and/or the test fluid.

It is, therefore, an object at least certain preferred embodiments of the present invention:

to provide new, useful, unique, efficient, and effective devices and methods for testing fluid chemical concentrations with sensors and for calibrating sensors;

to provide such devices and methods with which testing or calibration time is minimized;

to provide such methods and devices which permit the measurement of multiple calibration points in a single cavity;

to provide such methods and devices for reducing the errors associated with prior art calibration techniques;

to provide such devices and methods with which cleanliness or sterility can be maintained during calibration;

to provide such devices and methods useful with gas or liquid;

to provide such devices and methods which do not require that a gas be bubbled through a liquid;

to provide such devices and methods useful with optical sensors; and to provide such devices and methods for the use of and calibration of optical fiber blood gas sensors.

Calibrators according to the present invention can be used with the sensors disclosed in pending U.S. patent application Ser. No. 07/526,822 filed on May 22, 1990 and entitled "Optical Probe" which is incorporated herein for all purposes and a copy of which is submitted with the application for this patent.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

FIG. 1a is a cross-sectional view of a test container according to the present invention. FIG. 1b is an exploded view of the device of FIG. 1a.

FIG. 2a is a side view partially in cross-section of a calibrator according to the present invention.

FIG. 2b is a partial top view of the calibrator of FIG. 2a.

FIG. 3a is a side view partially in cross-section of a calibrator according to the present invention.

FIG. 3b is a partial top view of the calibration of FIG. 3a.

FIG. 4a is a side view partially in cross-section of a calibration system according to the present invention.

FIG. 4b is a cross-sectional side view of the fluid exchange chamber of the device of FIG. 4a.

FIG. 5a is a cross-sectional view of a calibrator according to the present invention.

FIG. 5b is a side view of the calibrator of FIG. 5a.

FIG. 5c is a top view of the calibrator of FIG. 5a.

DESCRIPTION OF EMBODIMENTS PREFERRED AT THE TIME OF FILING FOR THIS PATENT

Referring now to FIGS. 1a and 1b a calibration device 10 according to the present invention has a body 11 including a first body member 12 and a second body member 13. A female luer connector (not shown) maybe formed integrally of or secured to a top of the first body member 12 A channel 16 extends through the first body member 12. A cap (not shown) maybe removably secured at the top opening of the channel 14 or at the top of a female luer connector.

A microporous tube 20 is secured at a bottom opening 18 of the channel 16 and a channel 21 through the tube 20 communicates with the channel 16. The end of the tube 20 is sealed shut, e.g. by melting the end of the tube or with an adhesive 26 such as Dow Corning Silastic (TM) adhesive or Adhesive No. 4481 of the Electrolyte Corporation (an ultraviolet curable adhesive). Threads 24 are provided on a bottom end 19 of the first member 12. The channels 16 and 21 are sized for receiving a probe or sensor. It is preferred that the diameter of these channels be minimized so that equilibration of the sensor probe with the fluid used is achieved as quickly as possible. In one embodiment the tube channel 21 is about 1 millimeter in diameter and has a wall thickness of about 0.2 millimeters.

The second body 13 has a cavity 30 therein for receiving the tube 20 and into which and from which a known gas flows. Threads 32 on the second body member mate with the threads 24 to secure the two pieces together. Of course, it is within the scope of this invention to fabricate the body 11 from a single piece of material.

Gas is introduced into the cavity 30 through an inlet 34 and gas exits the cavity through outlets 36 (one shown). In another embodiment a gas outlet extends from the bottom end of the first body member 12 upwardly to an exit point of the first body member.

In use a device 10 with the body members secured together has the channels 16 and 21 filled with a fluid, e.g. a physiological buffer solution, and then a sensor probe (e.g., a probe of a blood gas sensor system) is inserted into the channels so that its sensor end is disposed in the tube 20. Then a gas of known concentration is introduced into and fills the cavity 30 through the inlet 34. Some of the gas permeates the microporous material of the tube 20 and diffuses into the fluid in the channel 21 which in turn affects sensor material in the sensor probe. A signal is sent from the probe to its associated system, the signal corresponding to the level of concentration of the gas. With an embodiment as described above, equilibration (the point at which chemical concentrations around the probe are at a substantially constant level) has been in about 20 minutes. It is preferred that equilibration be reached in at least about 30 minutes.

To then calibrate the probe with respect to another gas or the same gas at different concentration, the new gas is introduced into the cavity 30, equilibration is attained, and another measurement reading is taken and recorded. Output readings corresponding to known gas concentrations can be adjusted as desired to indicate the true concentrations of analytes in unknown samples.

It is preferred that the microporous material be thin silicone rubber, nitrocellulose, or an expanded polymer such as expanded Teflon (TM) material, expanded polyethylene, or expanded polypropylene In the embodiment of FIG. 1 it is preferred that the wall thickness of the material of the tube 20 be between about 0.025 millimeters to about 0.2 millimeters. It is within the scope of this invention to flow a liquid into the cavity 30 and to utilized a membrane that permits only certain ions or chemicals in the liquid (e.g., but not limited to sodium, blood enzymes, potassium) to pass through to affect a sensor probe.

Referring now to FIGS. 2a and 2b, in a calibrator 210 according to the present invention, compressed gas mixtures are allowed to flow alternately from reservoirs 211 and 212, controlled by a valve 203, through gas permeable microtubes 204 contained in cartridge 205. Top and bottom ends of the tubes can be sealed and adhered together with an adhesive. The microtubes 204 surround space at the end of a static reservoir 206. A probe 201 (e.g. an optical sensor probe) resides in a space in a container 207 with an inlet gas port 208 and a probe port 209. The probe is substantially parallel to a longitudinal axis of the tubes. Equilibration rate is affected by: the distance between the probe sensor site and gas stream; the interior of the microtubes and the permeability of the tubes. Final concentrations at chemical equilibrium are determined by the concentrations of the gases.

In this embodiment a fluid, e.g. a physiological buffer fluid 213, fills spaces between the microtubes 204 and the gas of known concentration flows through the microtubes and diffuses and dissolves into the fluid 213. The sensor probe, upon equilibration of the gas with the fluid, senses the concentration of the gas and conveys a signal indicating the level of concentration.

In the embodiment shown in FIGS. 3a and 3b, a calibrator 310 according to the present invention is like the calibrator 210, but an array of horizontally disposed (horizontal with respect to the microtubes of the calibrator 210) microtubes 304 is employed through which the known gas flows prior to contacting fluid in which a sensor probe 311 is disposed substantially normal to a longitudinal axis of the tubes. Items 301, 303, 305, 307, 308, 309, 311 and 312 correspond to items 201, 203, 205, 207, 208, 209, 211 and 212 respectively in FIG. 2a.

As shown, in FIGS. 4a and 4b, in a calibrator 410 according to the present invention compressed gases are allowed to flow from reservoirs 421 and 422 controlled by a valve 423 and to diffuse across a microporous membrane 424 which is contained in a gas exchange chamber 425. Calibration fluid 427 is circulated about a sensor probe 428 by means of a pump device, e.g. a diaphragm pump 429. The calibration fluid 427 flows in a channel 430 which extends through the chamber 425 and which communicates with the pump 429. The sensor probe 428 is sealingly disposed through an opening 431 in a housing 432 of the device. Gas exits the chamber 425 through a gas outlet 433.

Referring now to FIGS. 5a, 5b, and 5c, a calibrator 530 according to the present invention has an outer body 531 with a pleated hydrophobic microporous element 532 disposed therein. A female luer connector 533 is sealingly secured in an opening 534 of the body 531. A probe (not shown) may be inserted into the plug 533 and into a channel 535 in the pleated microporous hydrophobic membrane element 532. Gas of a known concentration is introduced into the body 531 through a hole 536 to diffuse across the element 532 and interact with the sensor probe. Gas exits from the body 531 through a hole 537.

Of course it is within the scope of this invention to utilize any of the devices disclosed, including but not limited to the preferred embodiments, for testing a fluid of unknown chemical concentration before or after calibrating a sensor by using a fluid of known concentration.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A test container for a probe of a sensor for sensing chemical concentration of a chemical from a second fluid in a first fluid, the test container comprising
    a body member having a cavity therein,
    a permeable means disposed in the cavity between the first fluid and the second fluid, the permeable means comprising a plurality of microporous tubes,
    an opening in the body through which the probe is insertable into the first fluid,
    at least one inlet in the body member through which the second fluid is introducible into the cavity for passing through the permeable means into the first fluid, and
    at least one outlet through which a portion of the second fluid which does not pass through the permeable means flows out from the cavity.

2. The test container of claim 1, wherein the probe is inserted substantially parallel to a longitudinal axis of the microporous tubes.

3. The test container of claim 1, wherein the probe is inserted substantially normal to a longitudinal axis of the microporous tubes.

* * * * *